United States Patent [19]

Nishimura et al.

[11] 4,435,570
[45] Mar. 6, 1984

[54] 5-(PHENYL OR BENZYL AMINO)METHYL-PYRROLO[2,3-D]PYRIMIDIN-4-ONE

[75] Inventors: Susumu Nishimura, Ichihara; Hiroshi Akimoto, Kobe, both of Japan

[73] Assignee: Takeda Chemical Industries, Ltd., Osaka, Japan

[21] Appl. No.: 423,249

[22] Filed: Sep. 24, 1982

[30] Foreign Application Priority Data

Sep. 26, 1981 [JP] Japan .................. 56-152646

[51] Int. Cl.$^3$ ................ C07D 487/04; A61K 31/505; A61K 43/00
[52] U.S. Cl. .................... 544/280; 424/1.1; 424/251
[58] Field of Search ......................... 544/280

[56] References Cited

U.S. PATENT DOCUMENTS 3,598,824  8/1971  Troxler et al. ............ 544/280
3,657,245  4/1972  Borman et al. ............ 544/280
4,229,453  10/1980  Roth et al. ............... 424/251

FOREIGN PATENT DOCUMENTS 312366  5/1959  United Kingdom ........... 544/280

OTHER PUBLICATIONS

S. Nishimura et al., GANN Monograph on Cancer Research, 24, 245–262 (1979).
J. R. Katze et al., Biochem. Biophys. Res. Comm., 96, 313–319 (1980).

Primary Examiner—Donald G. Daus
Assistant Examiner—S. A. Gibson
Attorney, Agent, or Firm—Wegner & Bretschneider

[57] ABSTRACT

Novel 7-deazapurine derivatives of the formula:

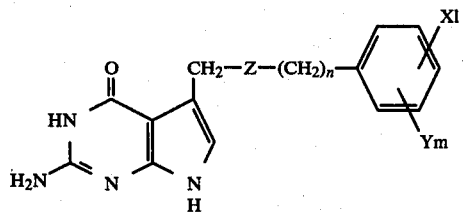

wherein X is halogen, Y is hydroxyl or di-$C_{1-3}$ alkylamino, Z is a —NH— or —NHC(=NH)— group, l is an integer of 1 to 5, m is an integer of 0 to 2, and n is 1 when Z is a —NH— group or n is 0 or 1 when Z is a —NHC(=NH)— group, and salts thereof are selectively taken up by tumor cells.

9 Claims, No Drawings

5-(PHENYL OR BENZYL AMINO)METHYL-PYRROLO[2,3-D]PYRIMIDIN-4-ONE

This invention relates to novel 7-deazapurine derivatives.

Establishment of exact and quick diagnosis of malignancy at an early stage is an important step in combatting human tumor. Malignancy diagnosis, an urgent and important problem, has been a subject of intensive investigation by a great number of researchers and a large volume of data has been collected. However, despite years of efforts, any generally applicable and effective methods of early malignancy diagnosis have not been found as yet.

The present inventors have found that Q base derivatives having the 7-deazaguanine skeleton show very high accumulability in various tumors including premalignant conditions and that the site, shape, size and presence or absence of a tumor tissue, for instance, can be described exactly by scanning with a scintiscanner following administration of such compounds labeled with a radioactive isotope to an organism. In other words, they have found that radioactive halogen-labeled Q base derivatives are useful compounds applicable in malignancy diagnosis and this finding has led to the present invention.

Q bases and related compounds [e.g. pre $Q_1$ base (7-aminomethyl-7-deazaguanine), pre $Q_0$ base (7-cyano-7-deazaguanine)] each having the same skeletal structure as the compounds of the present invention are existing as the constituents of tRANs (tRNA$^{Tyr}$, tRNA$^{His}$, tRNA$^{Asp}$ and tRNA$^{Asn}$) and these Q-containing tRNAs are widely distributed among the animal, plant and microbe kingdoms. The Q bases occur as the first letter of an anticodon of the above-mentioned tRNAs and therefore supposedly have an direct influence on the functions of tRNAs, namely recognition of genetic information from mRNAs and conversion of the information into an amino acid sequence of a protein. They are thus very important from biological points of view.

Recent advances in the fundamental fields of research on tumor have more and more elucidated the structure of tRNAs and the role of the same in vital phenomena. One of the most important findings is that, unlike in normal cells, Q-deficient tRNAs are present in tumor cells and further that the presence of Q-deficient tRNAs is a universal fact observable in all the tumor cells. On the other hand, the presence of tRNA-guanine transglycosidase has been confirmed in tumor cells as well as in normal cells. It has been elucidated that, when Qs are given from the outside, Q-deficient tRNAs take up the Q bases into the prescribed positions and thereby return to normal tRNAs [Akira Nishimura et al., GANN Monograph on Cancer Research, 24, 245–262 (1979)].

The present inventors synthesized a variety of Q base derivatives (including isotope-substituted ones). As a result, they have found that those which meet the structural requirements mentioned hereinbelow can serve as substrates for tRNA-guanine transglycosidase and can be taken up selectively by tumor cells and that therefore administration of these to organisms followed by scintiscanning can give exact scintigrams of malignancy nests, further have found that a variety of Q base derivatives display excellent antitumor activity through this new mode of action, and have completed the present invention.

Thus, the invention provides novel 7-deazapurine derivatives of the formula

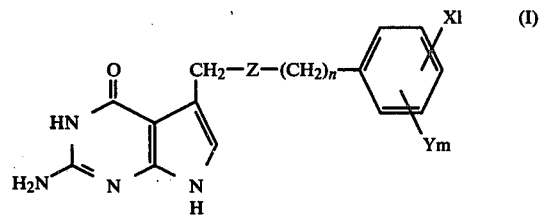

wherein X is halogen, Y is hydroxyl or di-$C_{1-3}$ alkylamino, Z is a —NH— or —NHC(=NH)— group, l is an integer of 1 to 5, m is an integer of 0 to 2, and n is 1 when Z is a —NH— group or n is 0 or 1 when Z is a —NH—C(=NH)— group, and salts thereof.

Referring to the above formula (I), the halogen represented by X includes, among others, iodine, bromine and chlorine atoms, which may contain radioactive isotopes, such as $$^{129}_{53}I, ^{131}_{53}I, ^{132}_{53}I, ^{133}_{53}I, ^{134}_{53}I, ^{135}_{53}I, ^{82}_{35}Br \text{ and } ^{38}_{17}Cl.$$

Among these radioactive isotopes, $$^{131}_{53}I$$

is especially preferred.

The di-$C_{1-3}$ alkylamino represented by Y includes, among others, dimethylamino, diethylamino.

The salts of compounds (I) include pharmaceutically acceptable salts, for example salts with inorganic acids such as hydrochloric acid, sulfuric acid, phosphoric acid and boric acid, and salts with organic acids, such as oxalic acid, tartaric acid, acetic acid, benzenesulfonic acid, p-toluenesulfonic acid and camphorsulfonic acid.

The compounds (I) of the invention are produced, for example by the following methods (A) and (B):

(A) The compounds of formula (I) wherein Z is a —NH—C(=NH)— group, namely 7-deazapurine derivatives of the formula

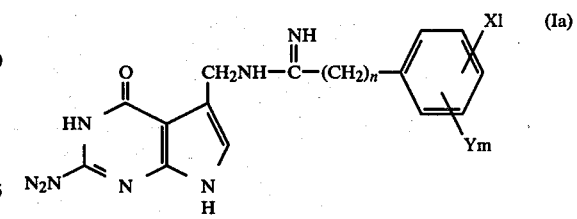

wherein each symbol is as defined above, are prepared by condensing a compound (pre $Q_1$) of the formula

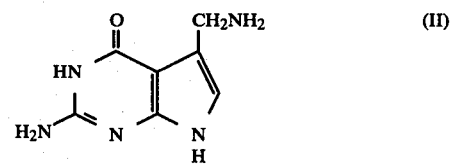

with a halogenated imidate of the formula

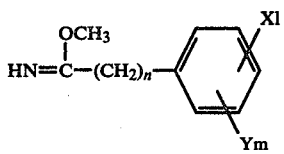

(III)

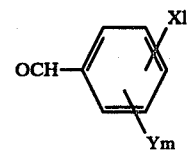

(IV)

wherein each symbol is as defined above.

Thus, compounds (Ia) can be produced by reacting pre $Q_1$ of formula (II) with a halogenated imidate of formula (III) or a mineral acid salt thereof (e.g. hydrochloride, sulfate, phosphate, nitrate, borate, hydrofluoride), either by themselves or in an appropriate solvent, at pH 2-14, normally at pH 6-13, at a temperature within the range of from −10° C. to the boiling point of the solvent, preferably within the range of 0°-50° C., for 1-100 hours. Compound (III) is used in an amount of 0.5-10 moles, normally about 1-3 moles, per mole of compound (II). Examples of the solvent are water, alcohols (e.g. methanol, ethanol), ether, tetrahydrofuran, dioxane, acetonitrile, ethyl acetate, dichloromethane, chloroform, acetone, dimethyl sulfoxide, dimethylformamide, benzene, toluene, and mixtures of these. The pH of the reaction mixture is adjusted as necessary with an acid (e.g. hydrochloric acid, sulfuric acid, phosphoric acid, nitric acid, acetic acid), a base (e.g. sodium hydride, sodium methylate, sodium ethylate, sodium hydroxide, potassium hydroxide, barium hydroxide, lithium hydroxide, sodium carbonate, potassium carbonate, barium carbonate, calcium carbonate, sodium hydrogen carbonate, trimethylamine, triethylamine, triethanolamine, pyridine) or a buffer solution (e.g. phosphate buffer, borate buffer, acetate buffer).

The starting compound (II) to be used in the above method can easily be prepared by a known method described in the literature [N. Okada et al., J. Biol. Chem., 254 3067 (1979)].

Another starting compound (III) includes known compounds and compounds prepared in a manner similar to known ones, such as 4-hydroxy-3,5-diiodobenzimidate, 4-hydroxy-3-iodobenzimidate, 2,4-dihydroxy-3,5-diiodobenzimidate, 2,5-dihydroxy-3,4,6-triiodobenzimidate, 3,4-dihydroxy-2,5,6-triiodobenzimidate, 4-hydroxy-3,5-dibromobenzimidate, 2,4-dihydroxy-3,5-dibromobenzimidate, 4-hydroxy-3,5-dichlorobenzimidate, 2,4-dihydroxy-3,5-dichlorobenzimidate and 4-hydroxy-3,5-diiodophenylacetoimidate.

In these starting compounds (III), the halogen may partly or wholly be replaced by radioactive isotopes.

(B) The compounds of formula (I) wherein Z is a —NH— group and n is 1, namely 7-deazapurine derivatives of the formula

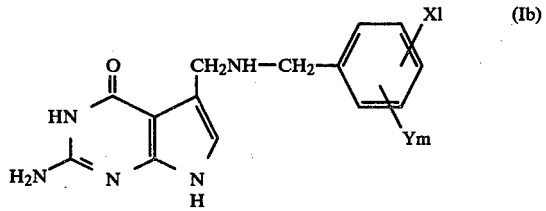

(Ib)

wherein each symbol is as defined above, are produced by condensing a compound of formula (II) with a halogenated benzaldehyde of the formula wherein each symbol is as defined above, and then reducing the resulting Schiff base of the formula

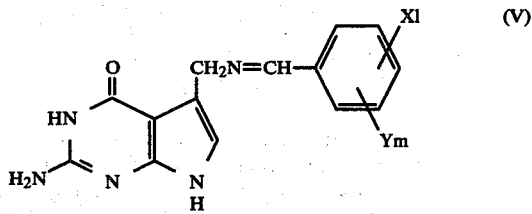

(V)

wherein each symbol is as defined above, or by directly condensing (II) with (IV) under reductive conditions without isolating (V).

Thus, compounds (V) are produced by reacting compound (II) with compound (IV) in a mole ratio of (IV)/(II)=about 3-0.5, either by themselves or in an appropriate solvent, at a temperature within the range of from −10° C. to the boiling point of the solvent, preferably within the range of 0°-50° C., for 10 minutes to 48 hours. In this reaction, compound (IV) may be used in the form in which the aldehyde moiety is protected as dimethyl acetal. Preferred examples of the solvent are nonaqueous solvents such as methanol, ethanol, n-propyl alcohol, isopropyl alcohol, ether, tetrahydrofuran, dioxane, acetonitrile, methyl acetate, ethyl acetate, dichloromethane, chloroform, carbon tetrachloride, dichloroethane, acetone, dimethyl sulfoxide, dimethylformamide, benzene, toluene and xylene. Addition of a dehydrating agent, such as a molecular sieve, calcium chloride, magnesium sulfate, sodium sulfate or calcium sulfate, may increase the rate of reaction and the yield. The resulting compound (V) can be isolated from the reaction mixture by a usual separation/purification method, such as concentration, solvent extraction, recrystallization and/or chromatography. The compound (V) formed in the reaction mixture may also be submitted directly to the subsequent reduction without isolation.

The reduction is carried out in the manner of catalytic reduction or reduction with a hydride, in an appropriate solvent, at a temperature within the range of from about −40° C. to the boiling point of the solvent, preferably within the range of about 0° C. to 50° C. Usable examples of the solvent are water, methanol, ethanol, n-propyl alcohol, isopropyl alcohol, ether, tetrahydrofuran, dioxane, methyl acetate, ethyl acetate, benzene, toluene, xylene, and mixtures of these. The catalyst for the catalytic reduction is, for example, palladium, platinum or rhodium. Furthermore, a small amount of acetic acid, hydrochloric acid, sulfuric acid or the like may be added and in this case compounds (Ib) are produced in the form of salts with such acids. In the reduction with a hydride, the reducing agent is, for example, lithium aluminum hydride, sodium borohydride, lithium borohydride or sodium cyanoborohydride. The reducing agent is used in amount of 1-100 moles, normally about 2-20 moles, per mole of the Schiff base.

The starting compounds (IV) to be used in this method are also known compounds or compounds producible in a similar manner and include, among others, 4-hydroxy-3,5-diiodobenzaldehyde, 2,4-dihydroxy-3,5-diiodobenzaldehyde, 4-hydroxy-3,5-dibromobenzaldehyde, 2,4-dihydroxy-3,5-dichlorobenzaldehyde, 4-iodobenzaldehyde and 4-bromobenzaldehyde.

Also in these starting compounds (IV), the halogen may partly or wholly be replaced by radioactive isotopes.

The compounds (I) of the invention thus produced can be isolated from the reaction mixture by a usual separation/purification method, for example concentration, solvent extraction, chromatography and/or recrystallization. Compounds (I) may also be isolated from the reaction mixture after conversion into the salt form mentioned above by a conventional method.

The 7-deazapurine derivatives (I) and pharmaceutically acceptable salts thereof according to the invention are, as above mentioned, taken up selectively by tumor cells. Therefore, when they are labeled with a radioactive isotope, for instance, they are useful, as radioactive medical agents, for malignancy diagnosis and they are useful for antitumor agent in tumor-bearing warm-blooded animals. In cases where they are used as such radioactive medical agents, radioactive compounds (I) are diluted with non-radioactive compounds (I) and/or per se known carriers or vehicles. In cases where compounds (I) are used as anti-tumor agent, they are used as they are or as formulated with pharmaceutically acceptable carriers, vehicles, diluents or the like. Compound (I) can be administered orally or parenterally in the form of pharmaceutical compositions such as injections, solutions, powders and capsules. In preparing capsules, for instance, compounds (I) are mixed with a carrier such as lactose or starch and placed in capsules (especially in case radioactive compound 1 mCi per capsule). In preparing injectable preparations, compounds (I) are dissolved or suspended in distilled water and the solutions or suspensions are placed in vials (in case radioactive compound 1 mCi per vial).

Compounds (I) have low toxicity and are accumulated specifically in tumor cells, and therefore have a high degree of safety as radioactive medical agents. In view of their properties, the radioactive medical agents containing compounds (I) should desirably be administered as soon as possible after preparation thereof. More specifically, in the case of administration to humans, the radioactive medical agents containing compounds (I) at a radioactivity of about 10 $\mu$Ci to 20 mCi are administered to subjects intravenously, intramuscularly or orally and then the site expected to have tumor or the whole body of each subject is examined with an appropriate device such as a scintillation scanner or a scintillation camera at adequate time intervals over about 0.5–100 hours, normally over about 1–50 hours. From the thus-obtained scintigrams, it is easy to diagnose the presence or absence, site, shape and size of tumor, and so on exactly and quickly.

When compound (I) is used as antitumor agent, the dosage depends on the subject animal species, disease, condition, the particular species of compound, route of administration, etc., the daily dose can be selected from the range of about 0.05 to 100 mg/kg body weight, preferably 0.1 to 10 mg/kg body weight.

The following examples and test results illustrate the invention in more detail. However, they are by no means limitative of the invention.

EXAMPLE 1

Production of 2-amino-5-[α-(3,5-diiodo-4-hydroxy)phenyliminomethylamino]methylpyrrolo[2,3-d]pyrimidin-4-one In a mixture of 5 ml methanol and 15 ml sodium borate buffer (pH 9.18) were dissolved 25.2 mg of 2-amino-5-aminomethylpyrrolo[2,3-d]pyrimidin-4-one(-dihydrochloride) and 44 mg of methyl 3,5-diiodo-4-hydroxybenzimidate(hydrochloride). The mixture was stirred at room temperature for 2 days. The reaction mixture was concentrated to dryness under reduced pressure and the residue was purified by silica gel column chromatography to give 22 mg of the desired compound.

Silica gel thin-layer chromatography (HPTLC, E. Merck, West Germany): Rf=0.61 (developing solvent: n-butanol saturated with conc. NH$_4$OH.)

NMR(CDCl$_3$—CD$_3$OD, 60 MHz) δ: 4.63(b-s,1H), 6.80(s,1H), 7.87(s,2H).

IR(KBr) ν: 3350, 3125, 1650, 1620, 1600 cm$^{-1}$.

EXAMPLE 2

Production of radioactive 2-amino-5-[α-(3,5-diiodo-4-hydroxy)phenyliminomethylamino]methylpyrrolo[2,3-d]pyrimidin-4-one in the same manner as Example 1, 4.4 mg of radioactive methyl 3,5-diiodo-4-hydroxybenzimidate hydrochloride (10 mCi, Japan Isotope Association) was reacted with 2.52 mg of 2 mg of 2-amino-5-aminomethylpyrrolo[2,3-d]pyrimidin-4-one (dihydrochloride) to give 2.2 mg (4 mCi) of the desired compound. The TLC, NMR and IR data on this compound were in complete agreement with the respective data on the same compound produced in the cold state.

This product was stored as diluted with a suitable carrier (e.g. the non-radioactive compound of Example 1).

EXAMPLE 3

Production of 2-amino-5-(p-iodobenzyl)aminomethylpyrrolo[2,3-d]pyrimidin-4-one

In 40 ml of dry methanol were suspended 126 mg of 2-amino-5-aminomethylpyrrolo[2,3-d]pyrimidin-4-one (dihydrochloride) and 116 mg of p-iodobenzaldehyde. After addition of 1 N methanolic sodium methoxide, the mixture was stirred at room temperature for 30 min. To this mixture was added 76 mg of sodium borohydride and the reaction was conducted at room temperature for 15 min. The reaction was then terminated by addition of 500 mg silica gel. The solvent was distilled off under reduced pressure and the residue was purified by silica gel chromatography to give 121 mg of the desired compound.

Silica gel thin-layer chromatography (HPTLC, Merck): Rf=0.6 (developing solvent: n-butanol saturated with conc. NH$_4$OH).

NMR(CD$_3$OD—C$_5$D$_5$N, 60 MHz) δ: 4.20(s,2H), 4.32(s,2H), 6.87(s,1H), 7.22(d,2H), 7.67(d,2H).

IR(KBr) ν: 3400, 3145, 2920, 1675, 1635, 1600, 1585 cm$^{-1}$.

EXPERIMENTAL EXAMPLE 1

Intake of the compound of Example 1 into tRNA

[$^3$H]guanine-labeled tRNA* (8000 cpm), 70 mM Trishydrochloride, 60 mM magnesium chloride, 0.5 unit of rat liver tRNA-guanine transglycosidase and 0.02 OD$_{260}$ of the compound of Example 1 were adjusted to 100 μl and reacted at 37° C. for 17 hrs. The reaction mixture was absorbed into a strip of Whatman 3 MM filter paper and washed three times with a 5% aqueous solution of trichloroacetic acid, once each with ethanol-ether (1:1) and ether. After drying, the paper strip was scanned with a toluenic scintillant. It was found that the compound of Example 1 had been taken into 59% of tRNA.

* tRNA labeled with [$^3$H] guanine in the first letter of its anticodon.

EXPERIMENTAL EXAMPLE 2

Intake of the radioactive compound of Example 2 into a tumor tissue

Using S-180 cancer-bearing mice (ddN mice, 10$^7$ tumor cells/mouse as transplanted i.p.), 100 mg (0.17 mCi)/kg of the radioactive compound of Example 2 was administered into the tail vein once. Twenty-four hours after administration, the animal was sacrificed and the tumor cells were taken out and the rate of takeup of the radioactive compound into tRNA in the tumor cells was determined. It was found that almost 100% of tRNA had been substituted by the radioactive compound. [Experimental method: N. Okada et al., Biochem., 19, 395 (1980)]

EXPERIMENTAL EXAMPLE 3

The 0.02 OD$_{260}$ equivalent of the compound of Example 3 was adjusted to 100 μl and subjected to the same procedure as Experimental Example 1. It was found that the compound had been taken into 93% of tRNA.

EXPERIMENTAL EXAMPLE 4

Inhibitory effect upon the multiplication of tumor cells

The inhibitory effect of compound (I) upon the multiplication of cells was detected using L5178Y cells (tumor cells) in RPMI 1640 medium+10% fetal calf serum for 48 hours at 37° C.

The result was expressed in the concentration of the drug giving a cell count of 50% (ED$_{50}$) with the average number of cells for the control (not modicated) group on the 2nd day being taken as 100%.

| Compound (Example No.) | ED$_{50}$ (μg/ml) |
|---|---|
| Q base | >200 |
| 1 | 20 |
| 3 | 35 |

What is claimed is:

1. A compound of the formula:

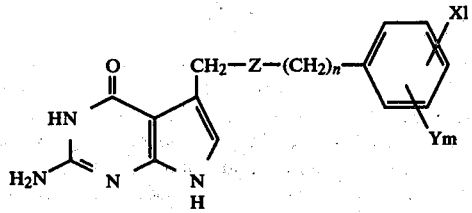

wherein X is halogen, Y is hydroxyl or di-C$_{1-3}$ alkylamino, Z is a —NH— or —NHC(=NH)— group, l is an integer of 1 to 5, m is an integer of 0 to 2, and n is 1 when Z is a —NH— group or n is 0 or 1 when Z is a —NHC(=NH)— group, or a pharmaceutically acceptable salt thereof.

2. The compound according to claim 1, wherein Z is a —NH— group.

3. The compound according to claim 1, wherein Z is a —NHC(=NH)— group.

4. The compound according to claim 1, wherein X is iodine.

5. The compound according to claim 2, wherein l is 1 and m is 0.

6. The compound according to claim 3, wherein l is 2, m is 1 and n is 0.

7. The compound according to claim 1, wherein X is halogen containing a radioactive isotope thereof.

8. The compound according to claim 1, which is 2-amino-5-[α-(3,5-diiodo-4-hydroxy)phenyliminomethylamino]methylpyrrolo[2,3-d]pyrimidin-4-one.

9. The compound according to claim 1, which is 2-amino-5-(p-iodobenzyl)aminomethylpyrrolo[2,3-d]pyrimidin-4-one.

* * * * *